US012558456B2

(12) United States Patent
Kiss et al.

(10) Patent No.: US 12,558,456 B2
(45) Date of Patent: Feb. 24, 2026

(54) METHOD FOR PREPARING BIOLOGICAL TISSUE FOR SURGICAL IMPLANTATION

(71) Applicant: P+F PRODUCTS + FEATURES GmbH, Vienna (AT)

(72) Inventors: Katharina Kiss, Vienna (AT); Guilherme Agreli, Sao Paulo (BR)

(73) Assignee: P+F PRODUCTS + FEATURES GmbH, Vienna (AT)

( * ) Notice: Subject to any disclaimer, the term of this patent is extended or adjusted under 35 U.S.C. 154(b) by 1203 days.

(21) Appl. No.: 17/428,760

(22) PCT Filed: Feb. 6, 2020

(86) PCT No.: PCT/EP2020/053001
§ 371 (c)(1),
(2) Date: Aug. 5, 2021

(87) PCT Pub. No.: WO2020/161243
PCT Pub. Date: Aug. 13, 2020

(65) Prior Publication Data
US 2022/0072202 A1 Mar. 10, 2022

(30) Foreign Application Priority Data
Feb. 7, 2019 (EP) ..................................... 19155986

(51) Int. Cl.
*A61L 27/36* (2006.01)
*A61L 2/18* (2006.01)
(Continued)

(52) U.S. Cl.
CPC ........... *A61L 27/3625* (2013.01); *A61L 2/186* (2013.01); *A61L 2/206* (2013.01); *A61L 27/3687* (2013.01);
(Continued)

(58) Field of Classification Search
None
See application file for complete search history.

(56) References Cited

U.S. PATENT DOCUMENTS 5,413,798 A * 5/1995 Scholl ................. A61L 27/3687
424/722
8,007,992 B2 8/2011 Tian et al.
(Continued)

FOREIGN PATENT DOCUMENTS

WO 0141828 A1 6/2001
WO WO-2011160085 A2 * 12/2011 ......... A61L 27/3625

OTHER PUBLICATIONS

Mori, S., Sawai, T., Teshima, T., & Kyogoku, M. (1988). A new decalcifying technique for immunohistochemical studies of calcified tissue, especially applicable to cell surface marker demonstration. Journal of Histochemistry & Cytochemistry, 36(1), 111-114. https://doi.org/10.1177/36.1.3275709 (Year: 1988).*

(Continued)

*Primary Examiner* — Charles A Marmor, II
*Assistant Examiner* — Marc D. Honrath
(74) *Attorney, Agent, or Firm* — Vivacqua Crane, PLLC

(57) ABSTRACT

The present invention relates to a method for treating biological tissue and a biological tissue obtained by the treatment method, and specifically to a method for treating biological tissue so as to suppress the calcification, risk of biofilm adherent over pericardium and strength reduction of the tissue due to treatment. The invention is also directed to bioprosthesis and transcatheter heart valves containing the biological tissue.

13 Claims, 9 Drawing Sheets

(51) Int. Cl.
    *A61L 2/186*      (2026.01)
    *A61L 2/20*         (2006.01)
    *A61L 2/206*      (2026.01)

(52) U.S. Cl.
    CPC ....... *A61L 2400/02* (2013.01); *A61L 2430/20*
                  (2013.01); *A61L 2430/40* (2013.01)

(56)              References Cited

U.S. PATENT DOCUMENTS

| | | |
|---|---|---|
| 2001/0023372 A1 | 9/2001 | Chen et al. |
| 2008/0102439 A1* | 5/2008 | Tian ...................... A61F 2/2415 |
| | | 623/23.72 |
| 2009/0180965 A1* | 7/2009 | Freyman ............. A61L 27/3847 |
| | | 424/556 |
| 2011/0300625 A1 | 12/2011 | Paniagua et al. |
| 2018/0133365 A1 | 5/2018 | Dong et al. |
| 2019/0001023 A1* | 1/2019 | Ashworth ........... A61L 27/3687 |
| 2020/0214834 A1* | 7/2020 | Rzany ................. A61L 27/3625 |
| 2022/0151775 A1* | 5/2022 | Kiss ...................... A61F 2/2418 |
| 2022/0257834 A1* | 8/2022 | Agreli ................. A61L 27/3641 |
| 2022/0257835 A1* | 8/2022 | Agreli ................... A61L 31/005 |

OTHER PUBLICATIONS

Nehir Sucuet al: "The effect of ethylenediaminetetraacetic acid on calcific degeneration in bovine pericardium", Heart and Vessels, vol. 19, No. 2, Mar. 1, 2004, XP055610714, ISSN 0910-8327, DOI: 10.1007/s00380-003-0734-8.

* cited by examiner

METHOD FOR PREPARING BIOLOGICAL TISSUE FOR SURGICAL IMPLANTATION

CROSS REFERENCE TO RELATED APPLICATIONS

This application is a national stage application under 35 U.S.C. 371 of PCT Application No. PCT/EP2020/053001 having an international filing date of 6 Feb. 2020, which PCT application claimed the benefit of European Patent Application No. 19155986.3 filed 7 Feb. 2019, the entire disclosure of each of which are hereby incorporated herein by reference.

FIELD OF THE INVENTION

The present invention is directed at a method for treating biological tissue and a biological tissue obtained by the treatment method, and specifically at a method for treating biological tissue so as to suppress the calcification, risk of biofilm adherent over pericardium and strength reduction of the tissue due to treatment. The invention is also directed at bioprosthesis and transcatheter heart valves containing the biological tissue.

BACKGROUND OF THE INVENTION

Biological tissues are widely used to make prosthetic replacements for heart valves and blood vessels as well as for transcatheter heart valves. They are connective tissues comprising collagen as the main component. Among these tissues, bovine pericardium is one of the most widely employed. Pericardial tissue is the sac surrounding the heart which provides a natural barrier to infection for the heart and prevents adhesion to the surrounding tissue. The pericardium also serves mechanical roles, for example, by preventing over dilation of the heart, maintaining the correct anatomical position of the heart, and regulating the pressure to volume ratio in the left ventricle during diastole. The structure of the tissue determines its behaviour under loading in both conditions physiologic to the pericardium and as a prosthetic device.

However, biological tissues obtained from the abattoir, in particular porcine and bovine cadavers, begin to degrade immediately. Therefore, in order to be able to exploit biological tissues as clinical material this deterioration must be stopped. The aim is to prolong the material's original structural and mechanical integrity and remove or at least neutralize the antigenic properties attributed to these materials. Methods typically concentrate on creating new additional chemicals bonds between the collagen molecules. These supplementary links reinforce the tissue to give a tough and strong but non-viable material that maintains the original shape of the tissue. For this purpose, a biological tissue, such as e.g. bovine or porcine pericardium or a heart valve, is chemically treated to improve its mechanical performance and immunogenic properties, reduce thrombogenicity and degradation, preserve sterility, and prolong the allowable storage period.

Accordingly, it is of significant importance to select a method of treating a biological tissue used for implantation which makes the tissue be readily available to medical personnel with minimal preparation prior to surgery. This reduces the opportunities for error and also the implantation time.

Various studies are known in this context from the prior art, in which biological tissues were treated by different methods. Reference is made in this context to the following references:

US 2008/0102439 A1 is directed to the preparation or storage of biological tissues, in particular mammalian tissue, used for surgical implantation, wherein said preparation method comprises contacting the biological tissue with a non-aqueous treatment solution comprising a polyhydric alcohol, such as glycerol, and a C1-C3 alcohol, and removing a portion of the treatment solution from the solution-treated biological tissue. The tissue of the mammal is selected from the group consisting of pericardium, aortic and pulmonary roots and valves, tendons, ligaments, skin, dura and peritoneum.

US 2018/0133365 A1 introduced a preparation method of a dry animal-derived collagen fiber tissue material comprising the steps of rinsing of an animal-derived collagen fiber tissue material that has been treated with a crosslinking agent, immersion of the rinsed tissue material in a non-aqueous alcoholic solution for dehydration, successive immersion of the tissue material that has been dehydrated with the non-aqueous alcoholic solution in saccharide solutions of different gradients of concentrations for gradient dehydration, taking out and drying of the gradient dehydrated tissue material, hermetic packaging of the dried tissue material and sterilization.

US 2011/0300625 A1 describes a method of preparing a tissue, in particular a pericardium tissue, wherein the method comprises providing a section of tissue harvested from a mammalian organism, and causing osmotic shocking of the section of tissue by performing multiple rinses of the section of tissue with distilled water, and further rinsing the section of tissue with isopropyl alcohol and contacting the section of tissue with one of a formalin solution or a glutaraldehyde solution.

U.S. Pat. No. 5,413,798 discloses a process for preparing bovine pericard materials and the use of the materials thus prepared as transplants or implants in human medicine and veterinary medicine. In particular, said document describes the process for treating bovine pericard tissue comprising the steps of wet-chemical processing the pericard tissue, drying the pericard tissue and sterilizing the pericard tissue, wherein the wet-chemical processing comprises separating from the surface of said tissue any adherent fat and basal membrane, contacting said tissue with an aqueous alkaline solution, contacting said tissue with a solution of a metal-ion complexing agent containing disodium EDTA and contacting said tissue with an aqueous buffer solution having a pH of 4.5 to 6.0 and rinsing with water.

In another approach, WO 01/41828 describes a method for treating a biomaterial comprising contacting the biomaterial with an anticalcification treatment solution, said anticalcification treatment solution being selected from a group consisting of higher alcohol solutions, polyol solutions and polar aprotic organic solvent solutions.

Further, US 2001/0023372 A1 discloses a method of preparing a tissue component for dry storage comprising providing an animal tissue component, treating said tissue component with an aqueous treatment solution comprising a dimensional stabilizer such as glycerol or a derivative thereof, storing said treated tissue component in a container that is essentially free of liquid.

Accordingly, each of the above mentioned patent applications have been made to develop a biological tissue which can be used as bioprosthetic devices that can be stored dry before used for clinical applications. However, there are certain disadvantageous associated with the above mentioned tissue preparation methods. For example, upon implantation a biological tissue, especially aldehyde fixed tissue, is susceptible to the formation of degenerative calcific deposits. Calcification, in particular pathologic calcification, of soft biological tissues due to deposition of calcium phosphate mineral salts in an implanted tissue is undesirable and the deposition of the calcific deposits can have severe consequences on device performance. Calcification of implants can lead to stiffening, structural instability and ultimately to device failure.

Therefore, it is of significant importance to provide biological tissues having resistance to calcification, especially because heart valve diseases necessitate valve replacement surgery in over several hundred thousand people worldwide each year.

The majority of clinically available bioprosthetic heart valves are composed of stent-mounted glutaraldehyde-fixed bovine pericardial tissue. Glutaraldehyde fixation effectively crosslinks the collagen in the tissue and to a great extent eliminates the immunogenicity and thrombogenicity of the bioprosthesis. However, a large amount of bioprosthetic heart valves fail due to pathologic calcification of the valve causing tissue stiffening and tearing.

Accordingly, it is desirable to provide new anticalcification approach with improved efficacy and ease of use. Thus, there is a need for an effective method of imparting anticalcification properties to biological tissues used for surgical implantations that is not accompanied by deleterious effect and also provides improved mechanical characteristics of a biological tissue during its storage.

SUMMARY OF THE INVENTION

For this reason it is an object of the present invention to provide a new method for preparing biological tissue suitable for sterile dry storage, i.e. without being immersed into a liquid preservation solution. It is a further object of the present invention to provide a new method that makes available biological tissues for surgical implantations in as close to ready-to-use form as possible. It is a further object of the present invention to provide a method of treating biological tissue which reduces calcification of the biological tissue, risk of biofilm adherence over pericardium and providing improved mechanical properties to a bioprosthesis comprising the biological tissue.

This object is satisfied by a method comprising the features of claim 1. Specific embodiments of the invention are described in the dependent claims.

In this connection, in a first aspect of the present invention, a method of treating biological tissue is provided, comprising the steps of:

soaking of the biological tissue treated with a crosslinking agent with a saline solution;

contacting the soaked biological tissue with an aqueous solution comprising Hydrogen Peroxide;

contacting the biological tissue with an aqueous solution comprising PBS and EDTA;

contacting the biological tissue with a solution comprising glycerol, ethanol and EDTA; and contacting the biological tissue with a glycerol solution.

In one embodiment, the method further comprises steps (3a) and/or (5a) of contacting the biological tissue with ethanol within a concentration of at least 70% by volume.

Preferably, the crosslinking agent used according to the claimed method is glutaraldehyde, for example having a concentration selected in the range of 0.1% to 5.0% by volume.

It is preferred that the biological tissue according to the claimed method is bovine or porcine pericardium or a heart valve.

Advantageously the saline solution according to the claimed method is an aqueous solution comprising 0.9% of sodium chloride by volume.

It is preferred that the concentration of hydrogen peroxide in step (2) according to the claimed method is from 0.05 to 5.0% by volume.

It is preferred that a volume ratio of glycerol to ethanol in step (4) according to the claimed method is from 1:5 to 5:1.

Advantageously the concentration of EDTA in steps (3) and (4) according to the claimed method is of 0.01% to 10.0% by weight.

It is further preferred that the method further comprises the steps of (6) drying the biological tissue, (7) placing the biological tissue in a package, (8) sealing the package and (9) sterilizing the package.

Further preferably that the steps (1) to (9) are carried out in a continuous way, i.e. one after another or sequentially.

Preferably the sterilizing of the package comprising the biological tissue according to the claimed method is carried out by exposing the package to ethylene oxide gas.

It is further preferred that the steps (1) to (7) of the claimed method are carried out at a temperature of 10° C. to 25° C., preferably at a temperature of 15° C. to 25° C., more preferably at a temperature of 18° C. to 22° C.

Preferably the steps (4) and (5) of the claimed method are carried out while stirring for at least 60 minutes.

In a second aspect, the present invention relates to a biological tissue comprising a biological tissue prepared according to the claimed method.

In a third aspect, the present invention relates to the use of a biological tissue prepared according to the claimed method for surgical implantation as well as to the use of the biological tissue as a bioprosthesis and in transcatheter heart valves.

DETAILED DESCRIPTION OF THE INVENTION

Figure 1:
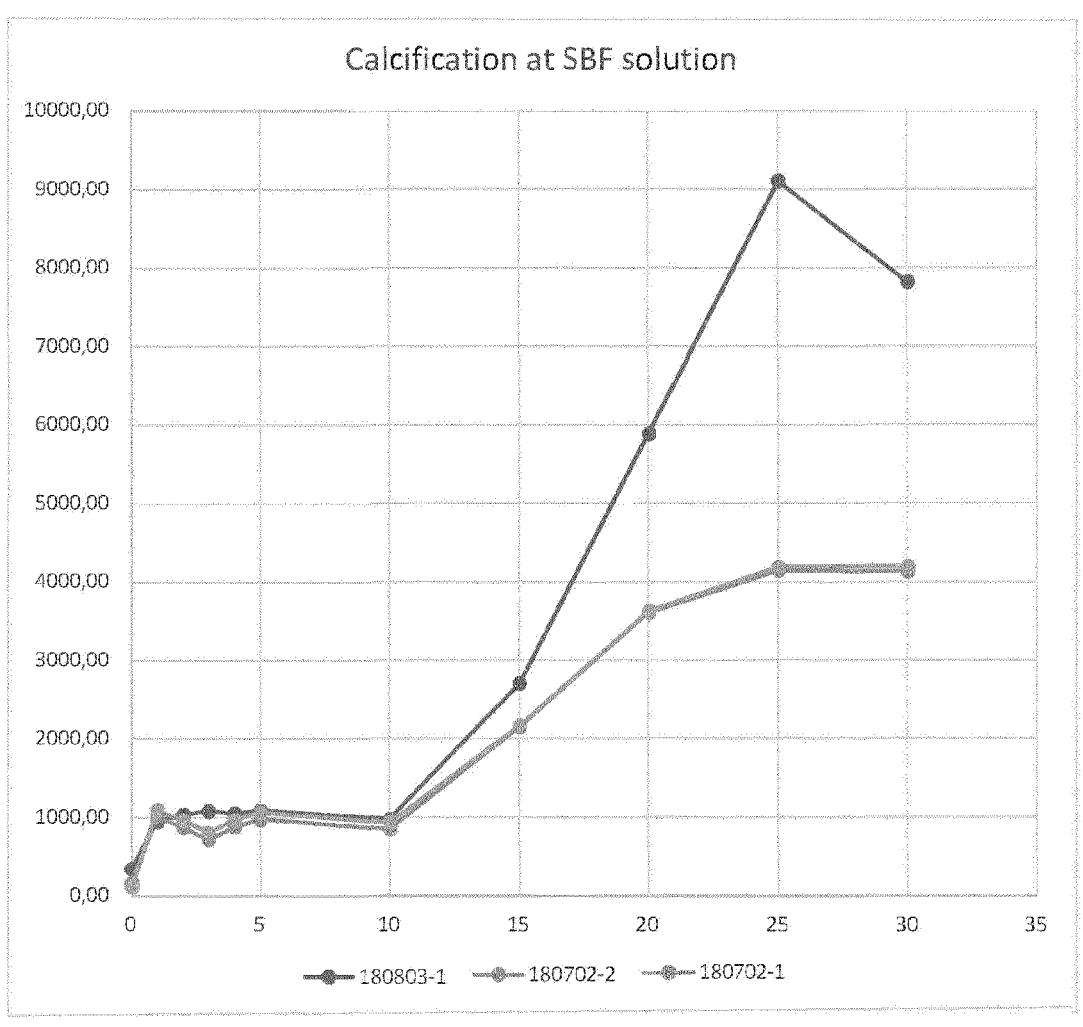
FIG. 1: Calcification of test bovine pericardium samples of examples 1-1 to 1-3.

In a first aspect, the present invention is directed at a method of treating biological tissue. Preferably, the method provides biological tissue containing such treated tissue in ready-to-use form for surgical implantations.

The term "biological tissue" is used herein to refer generally to treated or untreated collagen-containing biologically-derived human or animal materials.

In the present invention, it is preferably to use a pericardium or a heart valve as an animal biological tissue material, in particular obtained from a porcine or bovine heart, that has been treated with the crosslinking agent. The natural human heart valves are identified as the aortic, mitral, tricuspid and pulmonary valves. Pericardium tissue or heart valve tissues are used to replace damaged or diseased heart valves and to replace any of the above mentioned naturally occurring valves.

In this respect, the biological tissues produced according to the inventive method are used for construction of a "bioprosthetic device" or a "bioprosthesis" having a function much like a natural human heart valve, with the bioprosthetic imitating the natural action of the flexible heart valve leaflets. Tissue type heart valves are also significantly difficult and time consuming to manufacture, because they must be manufactured to exact standards and tolerances in order to function for years within the dynamic environment of a living patient's heart.

The primary component of the biological tissues is collagen. Collagen molecules consist of three chains of polyamino acids arranged in a trihelical configuration ending in non-helical carboxyl and amino termini. These collagen molecules assemble to form microfibrils, which in turn assemble into fibrils, resulting in collagen fibers. Because collagenous tissues degrade rapidly upon implantation into a host recipient, it is necessary to stabilize the tissue if it is to be used for clinical applications. Chemical stabilization by tissue cross-linking, also known as tissue fixation, has been achieved using a variety of compounds.

Most typically, chemical fixation has employed polyfunctional molecules having two or more reactive groups capable of forming irreversible and stable intramolecular and intermolecular chemical bonds with the reactive amino acid side groups being present on the collagen molecules.

The most widely used of these polyfunctional molecules is glutaraldehyde, which has an aldehyde at each end of a linear aliphatic chain. The aldehyde groups of glutaraldehyde and other like molecules react under physiological conditions with the primary amine groups of collagen molecules to cross-link the material. Glutaraldehyde cross linked tissue produced in this way exhibits increased resistance to enzymatic degradation, reduced immunogenicity and increased stability.

Despite its widespread use, there are certain disadvantages associated with tissue crosslinking with glutaraldehyde. For example, upon implantation, aldehyde fixed tissue is susceptible to the formation of degenerative calcific deposits, i.e. calcification. Calcification is the undesirable deposition of calcium phosphate mineral salts in an implanted tissue and is the most significant factor of failure of glutaraldehyde-fixed biological tissues used as biopros-thetic devices.

One embodiment of the present invention utilized soaking of the biological tissue treated with a crosslinking agent with a saline solution.

As used herein, a crosslinking agent is glutaraldehyde which is preferably used in biochemical and medicine applications as an amine-reactive homobifunctional cross-linker. As already mentioned above, glutaraldehyde treatment produces stable cross-links in cellular and extra-cellular matrix proteins which substantially reduced graft immunogenicity. However, such tissue has altered mechanical property, early mechanical failure, cytotoxicity, and incomplete suppression of immunological recognition. Besides this severe calcification was noticed in glutaraldehyde-treated bovine pericardium. An emerging alternative to glutaraldehyde treatment is further treatment according to the method of the present invention, i.e. a method allowing to reduce calcification of biological tissue.

In the present invention, it is preferably to use the crosslinking agent in an amount of from 0.1% to 5.0% by volume, more preferably from 0.2% to 3.0% by volume, further preferably from 0.3% to 2.0% by volume and especially preferably from 0.5% to 1.0% by volume.

In this respect, as a first step a soaking of the biological tissue with an aqueous saline solution comprising 0.9% of sodium chloride (9.0 g per litre) is carried out. Such a solution is also commonly named as normal saline, physiological saline or isotonic saline solution.

In a second step of the present invention, the soaked biological tissue is contacted with an aqueous solution comprising Hydrogen Peroxide. It is preferred that the concentration of hydrogen peroxide is from 0.05% by volume to 5.0% by volume, preferably from 0.1% by volume to 3.0% by volume, more preferably from 0.2% by volume to 2.0% by volume.

In a third step of the present invention, the biological tissue is contacted with an aqueous solution comprising PBS and EDTA.

As used herein, the term "contacting" means treating, immersion, exposing to, rinsing of the biological tissue used in the inventive method.

As used herein, the term "PBS" is directed to a phosphate buffered saline having a pH of 7.4 and containing water based salt solution of disodium hydrogen phosphate, sodium chloride and, in some formulations, potassium chloride and potassium dihydrogen phosphate. PBS is used in biological and medical applications, such as washing cells, transportation of tissues and dilutions, because PBS closely mimics the pH, osmolarity, and ion concentrations of the human body.

The term "aqueous solution" refers to a solution comprising a substance or a compound and water that has been purified to remove contaminants which are able to influence the end product. Preferably, distilled water, double distilled water or deionized water is used in a method of the present invention.

The term "EDTA" is used herein to refer to ethylenediaminetetraacetic acid which is a complexing chelating agent being able to sequester metal ions especially like $Fe^{2+}/Fe^{3+}$, $Al^{3+}$, $Mg^{2+}$, $Ca^{2+}$, $Mn^{2+}$, $Zn^{2+}$ and others and to remove them from the solution forming so called EDTA-complexes.

According to the present invention, it is especially important to remove calcium ions from the solution by forming calcium chelator that has been shown to inhibit mineralization of biological tissues, in particular bovine or porcine pericardium tissue. It is suggested that EDTA binds to calcium ions on the outer shell of hydroxyapatite crystals which are formed from calcium phosphate crystals thereby chelating and removing calcium ions from the crystals, causing the tissue material to shrink thus demineralizing the material.

Treatment of biological tissues with EDTA hence slows down the progression of calcification by binding calcium before it can react to form hydroxyapatite. Since the calcification of biological tissues used e.g. as bioprosthetic heart valves is a clinically significant problem that contributes to implant failure, it is of significant importance to reduce calcium level in biological tissues used as an implant. Therefore in the present invention, the EDTA treatment can reduce calcium level in biological tissues, especially in bovine or porcine pericardium or a heart valve preferably by 20%, more preferably by 30%, further preferably by 40% and especially preferably by 50%. Further, it is preferable to use EDTA in combination with PBS in order to increase demineralization and compatibility with a human body.

Further in the present invention, it is preferable to use EDTA, in particular in steps (3) and (4), having a concentration of more than 0.01% by weight, preferably of more than 0.05% by weight, more preferably of more than 0.10% by weight, still preferably of more than 0.15% by weight, and of less than 10.0% by weight, preferably of less than 8.0% by weight, more preferably of less than 6.0% by weight, still preferably of less than 5.0% by weight, further preferably of less than 3.0% by weight. Still further in the present invention, it is preferably to use disodium EDTA.

In a fourth step of the present invention, the biological tissue is contacted with a solution comprising glycerol, ethanol and EDTA, and in a fifth step the biological tissue is contacted with a glycerol solution in order to further reduce calcification of biological tissue and to dehydrate the biological tissue. The following steps describe an implementation of these processes in the method of the present invention.

After the biological tissues have been processed through steps (1) to (3) of the method of the present invention, they undergo the treatment in a solution comprising glycerol, ethanol and EDTA.

Phospholipids in and around biological tissue cells have been found the most prominent calcification nucleation sites. Therefore, the removal of these tissue components has been proposed to reduce mineralization, in particular calcification. Different studies have shown these to be effective calcification prevention strategies. The organic solvents like ethanol or glycerol or a mixture of ethanol and glycerol can be similarly used for this purpose. For example, the treatment with at least 70% ethanol, preferably with at least 80% ethanol, more preferably with at least 90% ethanol, extracts phospholipids from the tissue while also causing a change in collagen conformation that increases bioprosthesis resistance to collagenase. Thus, ethanol treatment allows extracting almost all phospholipids and cholesterols from the bioprosthesis, thus eliminating calcification of the biological tissue cells. Additionally, ethanol treatment also prevents adsorption of phospholipids and cholesterols from the solution. The method by which glycerol fixes biological tissue is not jet fully understood, but a 98% concentration, preferably 99% concentration, is sufficient to treat the biological tissue to make the tissue more biocompatible and resistant to calcification.

In this respect in the present invention, it is preferably to treat biological tissue in a solution comprising glycerol, ethanol and EDTA for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm. During this time most of the water molecules presented in biological tissue, in particular pericardial tissue, are replaced with glycerol.

Further in the present invention it is preferable to use a mixture of glycerol and ethanol, wherein a volume ratio of glycerol to ethanol is preferably from 1:5 to 5:1, more preferably from 1:4 to 4:1, still preferably from 1:3 to 3:1, further preferably from 1:2 to 2:1.

The biological tissues are then removed from the solution and placed in glycerol for further dehydration for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm.

Further in the present invention it is preferable to use an additional step of contacting or rinsing the biological tissue with ethanol having a concentration of at least 70% by volume, preferably with at least 80% by volume, more preferably with at least 90% by volume. The additional step, in particular step (3a), is preferably carried out before contacting the biological tissue with a solution comprising glycerol, ethanol and EDTA. It is further preferably to carry out another additional step (5a) of contacting the biological tissue with ethanol after the step of contacting the biological tissue with a glycerol and before the step of drying the biological tissue. It is still further preferably to carry out an additional step (3a) and/or (5a) using a mixture of ethanol and EDTA having a concentration as in step (3) or (4).

The biological tissues are removed from the solution and exposed to ambient air or an inert environment, e.g. nitrogen, at room temperature and humidity so as not to adversely affect tissue properties. Preferably, the drying is performed in a clean room at ambient conditions for at least 12 hours, preferably for at least 16 hours, still preferably for at least 20 hours. Further preferably, the drying is performed under high efficiency particulate air (HEPA) filter, in particular under HEPA conditions in a clean room. As used herein, the term "ambient conditions" is directed to the ambient temperature of more than 10° C., preferably of more than 12° C., more preferably of more than 14° C., especially preferably of more than 18° C., and preferably of less than 25° C., more preferably of less than 23° C., further preferably of less than 22° C. Further in the present invention it is preferably to carry out each of steps (1) to (7) at the ambient conditions as described above.

The treated and dried biological tissues are then packaged in a container or package essentially free of liquid for subsequent surgical implantation. As used herein, the term "essentially free of liquid" means a non-fluid environment in which the presence of water or other substances is limited to approximately the content of such substances in ambient air.

One preferred method is to apply a vacuum to the package to minimize the level of oxygen, and one may additionally utilize a backfill of an inert gas, such as nitrogen. Such methods of sterile packaging are known to those skilled in the art.

The packaged treated tissue can then be sterilized by a gaseous sterilization process or by an exposure to ionizing radiation. To ensure that the chamber remains sterile following sterilization, the package members are formed from a material that is impenetrable to micro-organisms such as bacteria and fungi. After the tissue or bioprosthetic device containing such tissue is placed in the chamber and/or sterilized, the chamber is sealed.

Sterilization by exposure to ionizing radiation or sterilizing gas, particularly by exposure to ethylene oxide gas, is within the skill of the art. In a preferred embodiment, biological tissues are sterilized by exposing the biological tissue to sterilizing gas, in particular to ethylene oxide gas (ETO). Sterilizing with ETO method is usually carried out at a temperature between 37° C. and 55° C., gas mixture comprising at least 10% of ethylene oxide and for at least 60 minutes.

The resulting product is a substantially sterile and sealed implantable tissue present in a substantially dry form. It is especially well-suited for surgical implantation into human patients for the treatment of any number of diseases or conditions. Prior to surgical implantation, the biological tissue is removed from the package, and the tissue component optionally rehydrated by exposure to an aqueous solution, preferably a sterile aqueous solution. The tissue can be rehydrated by multiple soakings in a sterile solution such as physiologic saline. The glycerol and ethanol in the tissue can be easily washed off by saline.

The described method provides a biological tissue having dimensional stability and which is essentially ready for surgical implantation into a patient, i.e. so called ready-to-use form.

Biological tissues treated in accordance with the method of the present invention will typically return to a size that is at least 95%, more preferably at least 97%, further preferably at least 99% of its original hydrated size. As a result, the biological tissues prepared in accordance with the inventive method are ready-to-use for surgical implantation as an implantable bioprosthetic device, in particular in transcatheter heart valves.

Further in the present invention it is preferably to use a pericardium or a heart valve as a biological tissue. Accordingly, the pericardium or heart valve tissue can be processed according to the method of the present invention prior to their use for surgical implantation. Still further in the present invention it is preferable to use a pericardium or a heart valve obtained from an animal tissue, in particular from a porcine or bovine heart. Preferably, the bovine pericardium obtained from a certified abattoir undergoes the procedures of cleaning, trimming and crosslinking with glutaraldehyde before the use in a method of the present invention.

The invention is further directed at bioprosthesis and transcatheter heart valves containing the biological tissue.

In one embodiment, the present invention relates to a biological tissue comprising a biological tissue prepared according to the claimed method.

In another embodiment, the present invention relates to the use of a biological tissue prepared according to the claimed method for surgical implantation as well as to the use of the biological tissue as a bioprosthesis and in transcatheter heart valves.

As used herein, the term "bioprostheses" means a device derived from processed biological tissue to be used for implantation into humans. The development of such devices originated as an attempt to circumvent some of the clinical complications associated with the early development of the mechanical heart valve, and has since resulted in a rapid proliferation of bioprosthetic devices for a variety of applications. Examples of some of the bioprostheses currently used or under development include heart valves, vascular grafts, biohybrid vascular grafts, ligament substitutes, pericardial patches and others.

The following examples are for purpose of illustration only and are not intended to limit the scope of the present invention as defined in the claims which are appended hereto:

Example 1-1

40 membranes with 1×1 cm of a biological tissue selected from bovine pericardium "sample 180702-1" (P+F Brasil, EDQM certified) has been at first removed from 0.625% glutaraldehyde solution (P+F GmbH/Biocollagen) and after that soaked in cold 0.9% saline solution (JP Pharma) for 3 minutes. The soaked tissue has then been immersed in Hydrogen Peroxide 0.5% per volume (Sigma-Aldrich) at 18° C. for 60 minutes. As a next step, the tissue was contacted with cold (10° C.) PBS pH 7.4 and 0.5% by weight EDTA for 3 minutes (Sigma-Aldrich). After that the tissue was immersed in 99% per volume ethanol (Sigma-Aldrich) at 22° C. temperature for 60 seconds with intense stirring, and then immersed in a mixture of glycerol/ethanol (50/50) and 0.5% by weight EDTA (Sigma-Aldrich) at 22° C. temperature for 60 minutes with slow stirring. Further, the tissue was immersed in glycerol 99% (Sigma-Aldrich) at 22° C. temperature for 120 minutes with slow stirring. Next, the tissue was soaked with absolute ethanol 99% per volume (Sigma-Aldrich) and 0.5% by weight EDTA at 22° C. temperature during 60 seconds with intense stirring. Finally, the tissue undergoes a procedure of solvent evaporation under HEPA filtered air insufflation during 18 hours at 18° C. temperature. Then, the tissue was packed at double Tyvek pouch and ETO sterilized (55° C., 4 hours ETO exposition) at Sterium Company.

Example 1-2

40 membranes with 1×1 cm of a biological tissue selected from bovine pericardium "sample 180702-2" has been prepared according to procedure described in Example 1-1.

Comparative Example 1-3

40 membranes with 1×1 cm of a biological tissue selected from bovine pericardium "sample 180803-1" has been removed from 0.625% glutaraldehyde solution (P+F GmbH/Biocollagen) and used as a comparative sample without further treatment.

Example 1-4

Bovine pericardium membranes from Examples 1-1 to 1-3 (number of samples: 180702-2 and 180702-1 are according to the present invention, and 180803-1 is a comparative example) were soaked in saline solution for 2 minutes and then immersed in a Simulated Body Fluid (SBF), which is a solution with ionic concentration similar to that of human blood plasma such as demonstrated in Table 3, maintained under the same physiological conditions of pH and temperature (pH 7.4 and temperature of 36.5° C.). The immersion time varied between 1 and 30 days.

The samples were digested in a closed flask conductive heating system called CHDS. The calibration curve was prepared from the Specsol® 1000 mg. L$^{-1}$ standard solution to contain 0.0-20 mg. L$^{-1}$ Ca.

The determination of Ca presented in Table 1 and FIG. 1 was performed on a ContrAA 300 High Resolution Continuous Source Atomic Absorption Spectrometer (HR-CS FAAS) (Analytic Jena, Jena, Germany), equipped with a short arc lamp of Xe as a continuous source of radiation (in FIG. 1 the sign "," on Y-axis has to be read as a point according to Table 1, i.e. the value 1000,00 has to be understood as 1000 or 1000.00).

Figure 2:
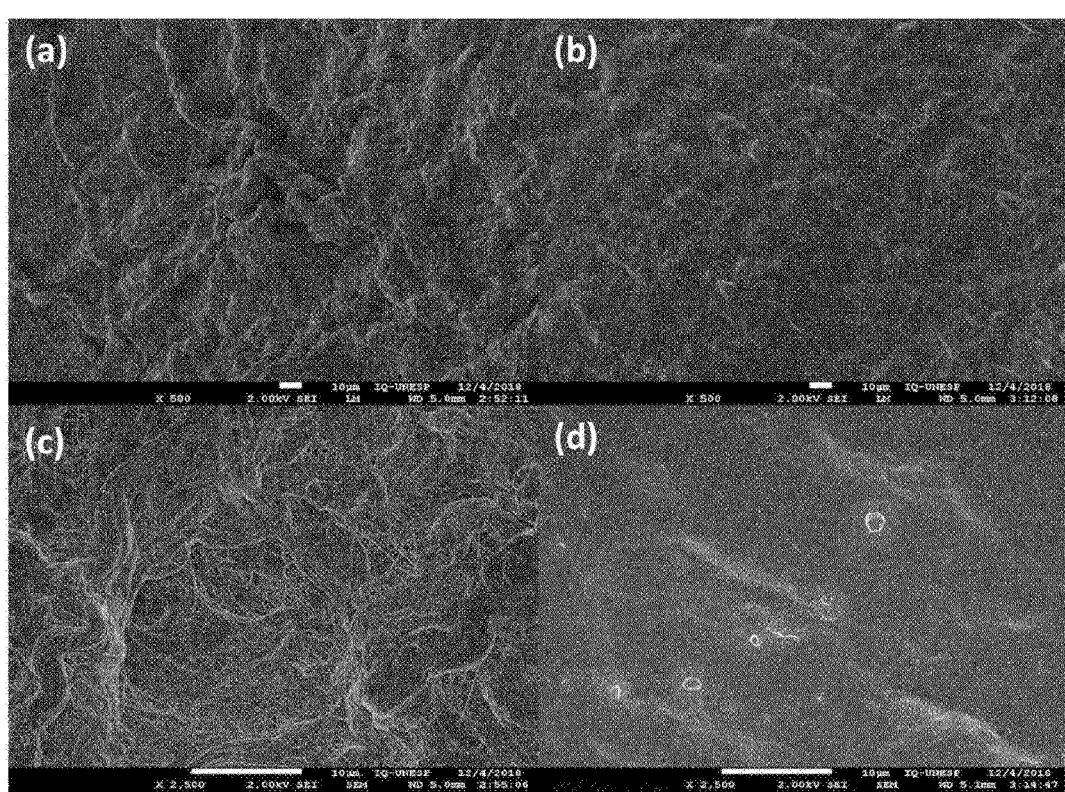
FIG. 2: Scanning Electron Microscope images (SEM) of the bovine pericardium: (a) and (c) without SBF, (b) and (d) immersed in SBF solutions for 24 hours.

Scanning electron microscope (SEM) was performed on the samples of bovine pericardium (180803-1 glutaraldehyde preserved) using a field emission scanning electron microscope (FESEM) (JEOL, model 7500F): (a) and (c) without SBF, (b) and (d) immersed in SBF solutions for 24 hours (see FIG. 2).

TABLE 1

| days | 180803-1 Ca mg/kg | 180702-2 Ca mg/Kg | 180702-1 Ca mg/kg |
|---|---|---|---|
| 0 | 342.44 | 170.95 | 114.17 |
| 1 | 951.35 | 1009.33 | 1095.72 |
| 2 | 1032.68 | 871.74 | 958.13 |
| 3 | 1080.46 | 719.87 | 806.27 |
| 4 | 1046.86 | 879.55 | 965.94 |
| 5 | 1088.43 | 974.26 | 1060.65 |
| 10 | 973.81 | 846.86 | 933.25 |
| 15 | 2703.91 | 2151.70 | 2165.84 |
| 20 | 5887.85 | 3607.95 | 3623.10 |
| 25 | 9100.73 | 4145.59 | 4186.11 |
| 30 | 7812.76 | 4123.35 | 4193.58 |

Example 2-1

75 units of a biological tissue selected from bovine pericardium (P+F Brasil) and fixed in the presence of glutaraldehyde (Sigma-Aldrich, 0.625% by volume) has been placed in a cold 0.9% saline solution (JP Farma) and after that in an aqueous solution comprising PBS (Sigma-Aldrich) of pH 7.4 and EDTA (Sigma-Aldrich, 0.2% by weight) for 3 minutes with following rinsing with ethanol (Sigma-Aldrich, 70% by volume). The soaked tissue has then been immersed in ethanol at an ambient temperature for about 1 minute. As a next step, the tissue was contacted with a mixture of glycerol (Sigma-Aldrich, 99%), ethanol and EDTA solution (70% Glycerol, 29.8% Ethanol and 0.2% EDTA solution) at an ambient temperature for at least 90 minutes. After that the tissue has been immersed in glycerol for at least 90 minutes while stirring and with following rinsing with ethanol. Then the tissue was carefully removed from the solution and dried by air. After 16 hours of drying the tissue was examined with regard to rehydration and mechanical stability.

Figure 3:
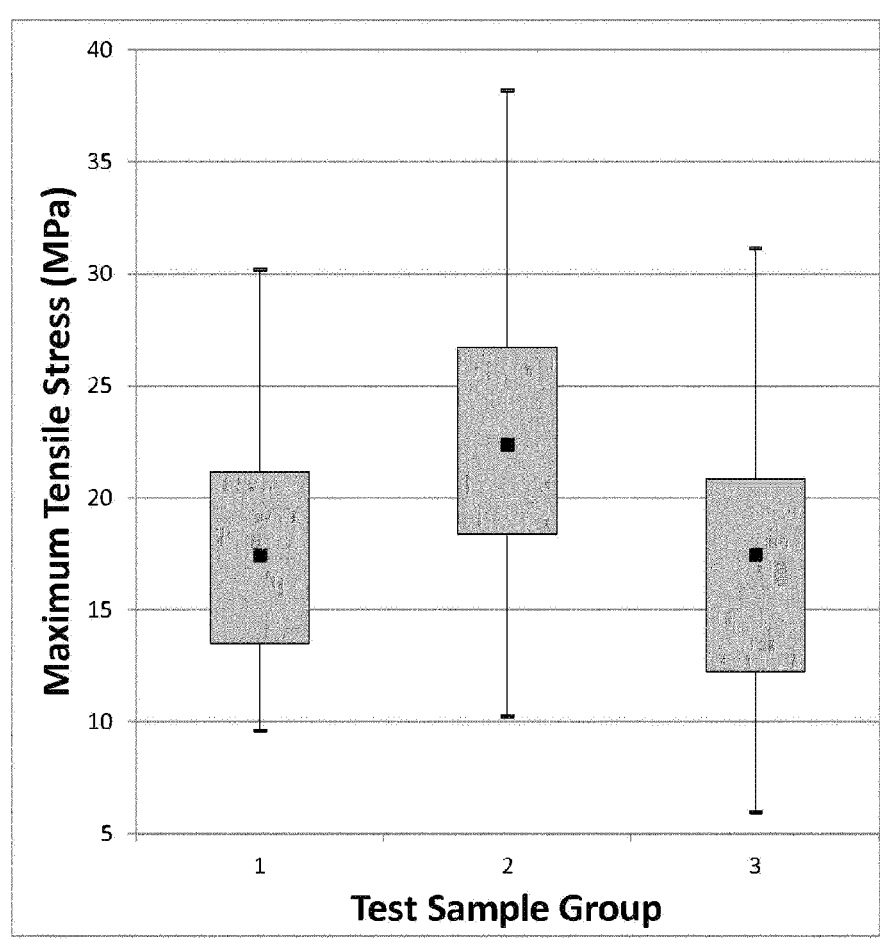
FIG. 3: Tensile strength of test bovine pericardium samples of different preparation steps.

The mechanical properties of a material, in particular tensile strength, were tested under strain-stress evaluation using Universal Testing Machine (Oswaldo Filizzola, model AME-2 kN). The tensile strength of the test bovine pericardium samples of different preparation steps is shown in FIG. 3, wherein group 1 corresponds to standard pericardium, group 2 corresponds to dry pericardium and group 3 corresponds to dried and rehydrated pericardium.

Example 2-2

04 (4 patchs circular with 130 mm diameter) units of a biological tissue selected from bovine pericardium (P+F Brasil) and fixed in the presence of glutaraldehyde (Sigma-Aldrich, 0.625% by volume) has been placed in a cold 0.9% saline solution (JP Farma) and after that in an aqueous solution comprising PBS (Sigma-Aldrich) of pH 7.4 and EDTA (Sigma-Aldrich, 0.2% by weight) for 3 minutes with following rinsing with ethanol (Sigma-Aldrich, 70% by volume) The soaked tissue has then been immersed in ethanol at an ambient temperature for about 1 minute. As a next step, the tissue was contacted with a mixture of glycerol (Sigma-Aldrich, 99%), ethanol and EDTA solution (70% Glycerol, 29.8% Ethanol and 0.2% EDTA solution) at an ambient temperature for at least 90 minutes. After that the tissue has been immersed in glycerol for at least 90 minutes while stirring and with following rinsing with ethanol. These samples were submitted to Atomic Absorbance Spectrometry ContrAA 300 (Analytik Jena, Jena, Germany). Table 2 demonstrates the calcium content of these samples to standard glutaraldehyde preserved bovine pericardium.

TABLE 2

| Sample | Conc. Ca (g/Kg) | Conc. Ca (ppm) |
|---|---|---|
| Dry | 0.0652 | 65.2 |
| Glutaraldehyde | 0.1452 | 145.2 |

To compare the calcium absorption of pericardium samples, the dried and standard pericardium samples were incubated in a Simulated Blood Solution (SBF) of an ionic concentration according to Table 3, which is similar to human blood plasma.

TABLE 3

| | Na$^+$ | K$^+$ | Ca$^{2+}$ | Mg$^{2+}$ | HCO$_3$$^{2-}$ | Cl$^-$ | HPO$_4$$^{2-}$ | SO$_4$$^{2-}$ |
|---|---|---|---|---|---|---|---|---|
| SBF (mg/L) | 213.0 | 7.5 | 3.8 | 2.3 | 6.3 | 223.0 | 1.5 | 0.75 |

The samples were incubated in SBF during 24 hours and after that submitted to Atomic Absorbance Spectrometry analysis. The results are demonstrated in Table 4.

TABLE 4

| Sample | Conc. Ca (g/Kg) | Conc. Ca (ppm) |
|---|---|---|
| Dry/SBF | 0.5446 | 544.6 |
| Glutaraldehyde/SBF | 0.8251 | 825.1 |

Example 2-3

The collagen fibre integrity was studied by histological evaluation using stain to examine the collagen fibre preservation after drying process in a bovine pericardium sample. The images have been obtained using Eclipse E-200 (Nikon) together with video digital full HD Lite 1080p (Tucsen). The results have been compared with a standard glutaraldehyde preserved material sample. The examination was made using different stains as demonstrated in FIG. 4 (dried bovine pericardium) and FIG. 5 (standard bovine pericardium), wherein HE means Hematoxylin, RE means Resorcine-Orcein, TM means Masson's trichrome and TG means Gomory's trichrome (all stains were provided by Merck).

Figure 4:
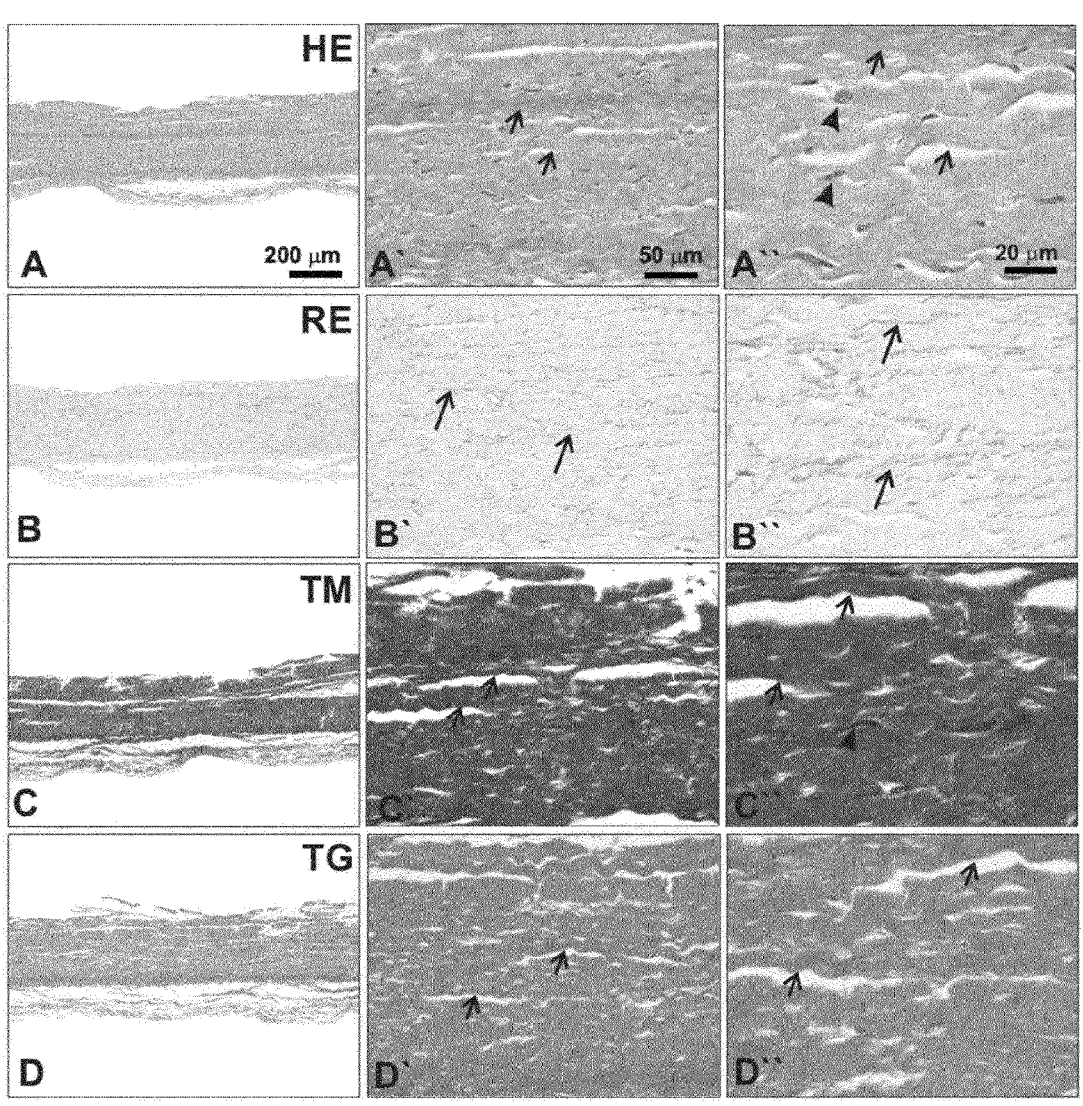
FIG. 4: An Optical Microscope (Eclipse E-200 Nikon with video digital full HD Lite 1080p Tucsen) image of histological evaluation using stain of a dried bovine pericardium sample.

FIG. 4 demonstrates a microscopic picture (without light field microscopy) of cross-sectional histological sections of the PF180611-Std 05 membrane stained by the hematoxylin and eosin (HE, A-A"), resorcinine-orcein (RE, B-B"), trichrome of Mallory (TM, C-C") and Gomori trichrome (TG, D-D"). The following parts of the dried bovine pericardium sample can be observed: the thick collagen fibers (smaller black arrows), elastic fibers in transverse or longitudinal sections (large black arrows), remnants of cell nuclei (arrowheads). There is no remnants of vascular elements presented in this picture. The scale shows the actual magnification of the photomicrographs.

Figure 5:
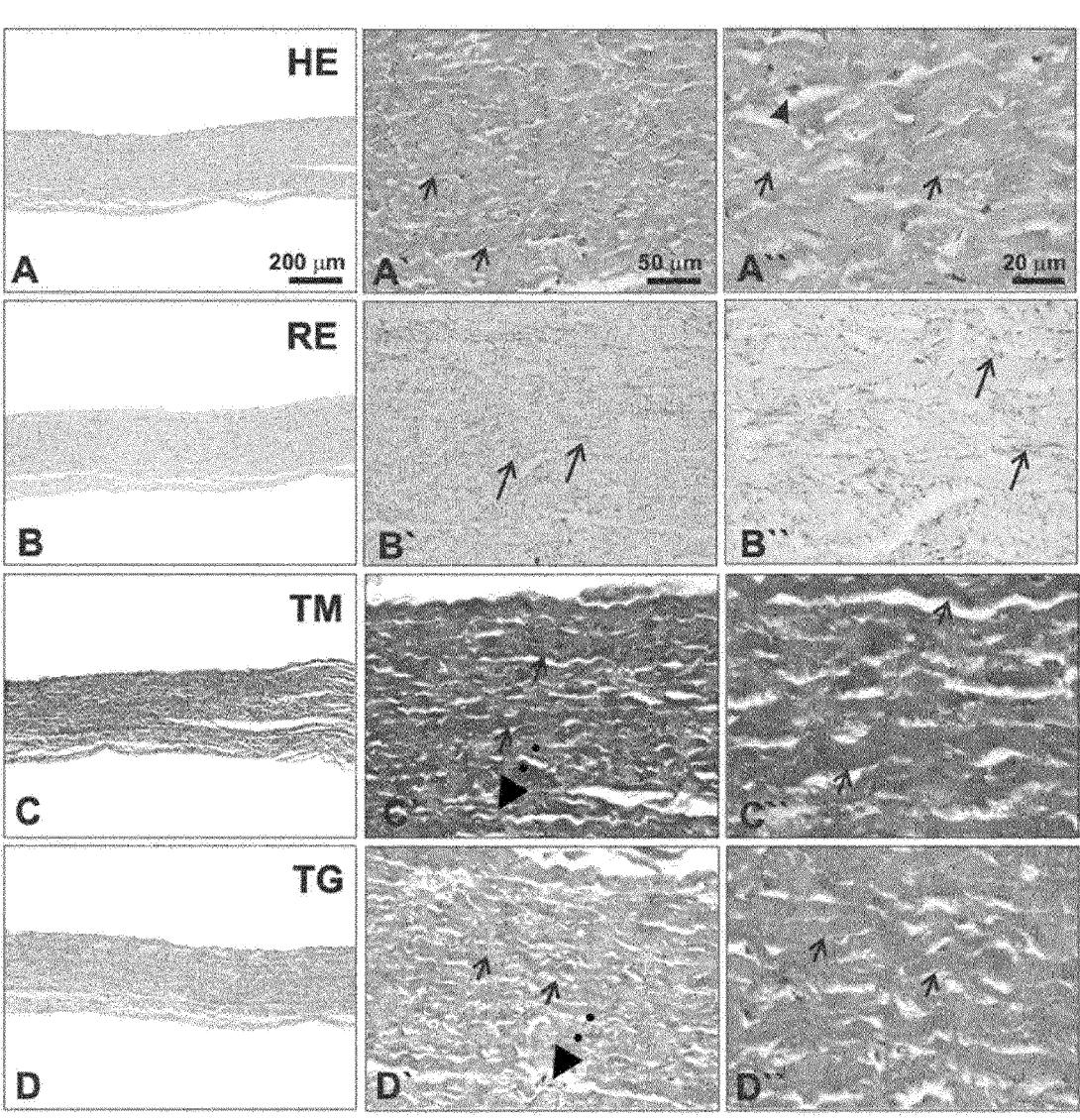
FIG. 5: An Optical Microscope (Eclipse E-200 Nikon with video digital full HD Lite 1080p Tucsen) image of histological evaluation using stain of a standard bovine pericardium sample.

FIG. 5. demonstrates a microscopic picture (without light field microscopy) of cross-sectional histological sections of the PF180801-3-DRY05 membrane stained by the hematoxylin and eosin (HE, A-A"), resorcinine-orcein (RE, B-B"), trichrome of Mallory (TM, C-C") and Gomori trichrome (TG, D-D"). The following parts of the standard bovine pericardium sample can be observed: the thick collagen fibers (smaller black arrows), elastic fibers in transverse or longitudinal sections (large black arrows), remnants of cell nuclei (arrowheads) and remnants of vascular elements (large head and pointed arrows). The scale shows the actual magnification of the photomicrographs.

Example 2-4

Figure 6:
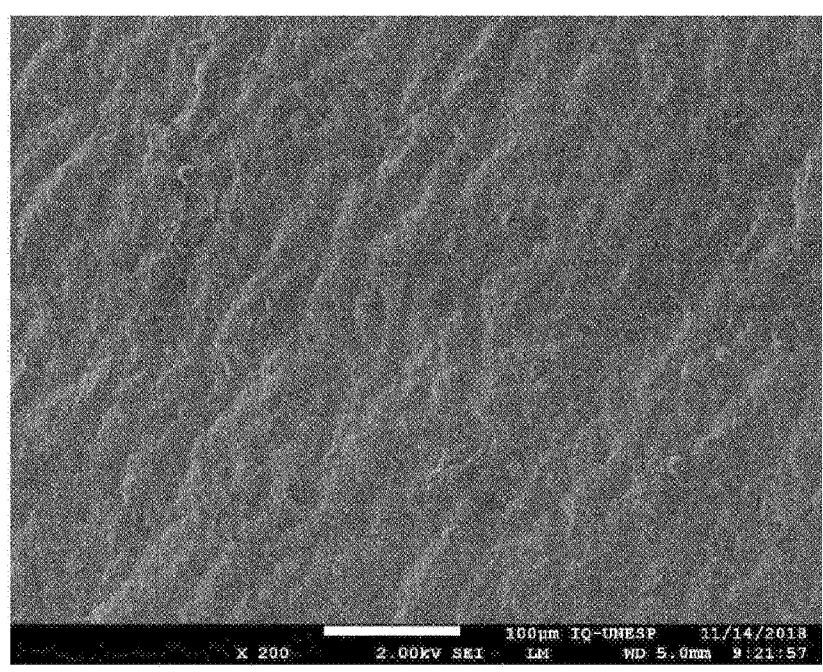
FIG. 6: A Scanning Electron Microscope image (200×) of a dried bovine pericardium sample.
Figure 7:
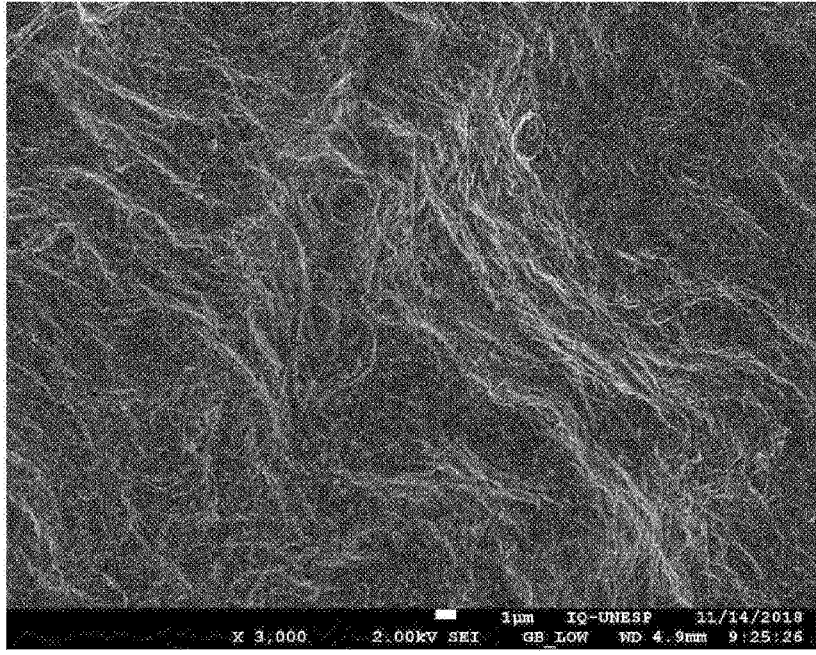
FIG. 7: A Scanning Electron Microscope image (3000×) of a dried bovine pericardium sample.
Figure 8:
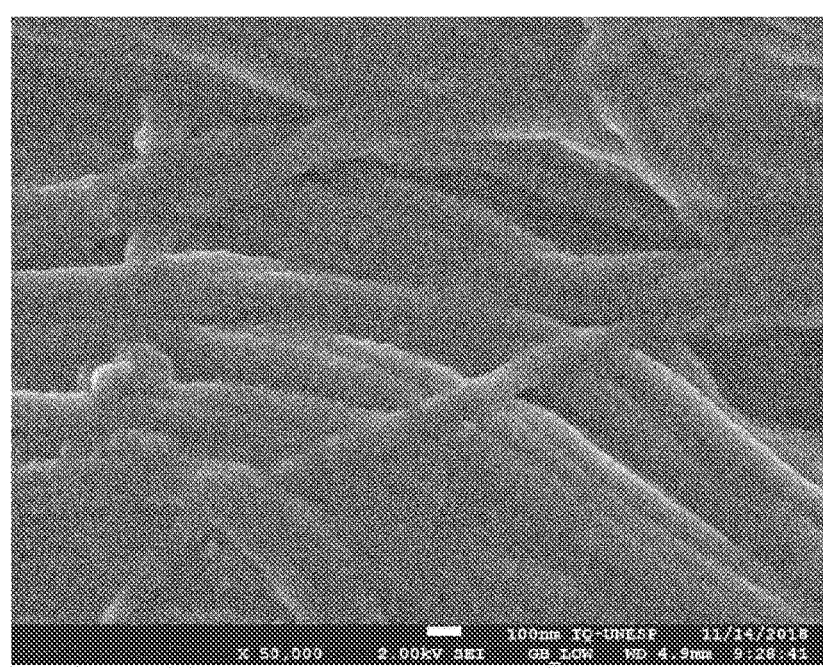
FIG. 8: A Scanning Electron Microscope image (50000×) of a dried bovine pericardium sample.
Figure 9:
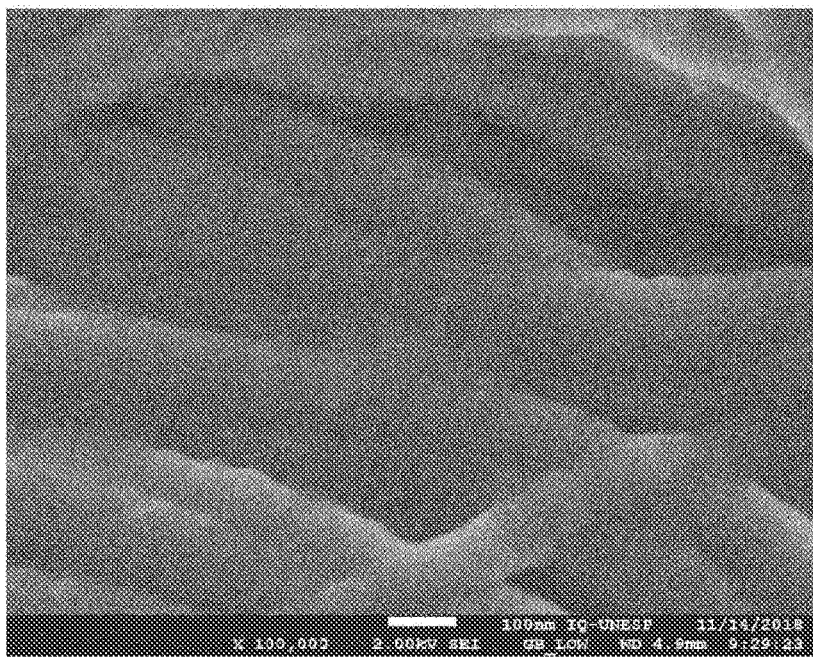
FIG. 9: A Scanning Electron Microscope image (100000×) of a dried bovine pericardium sample.
Figure 10:
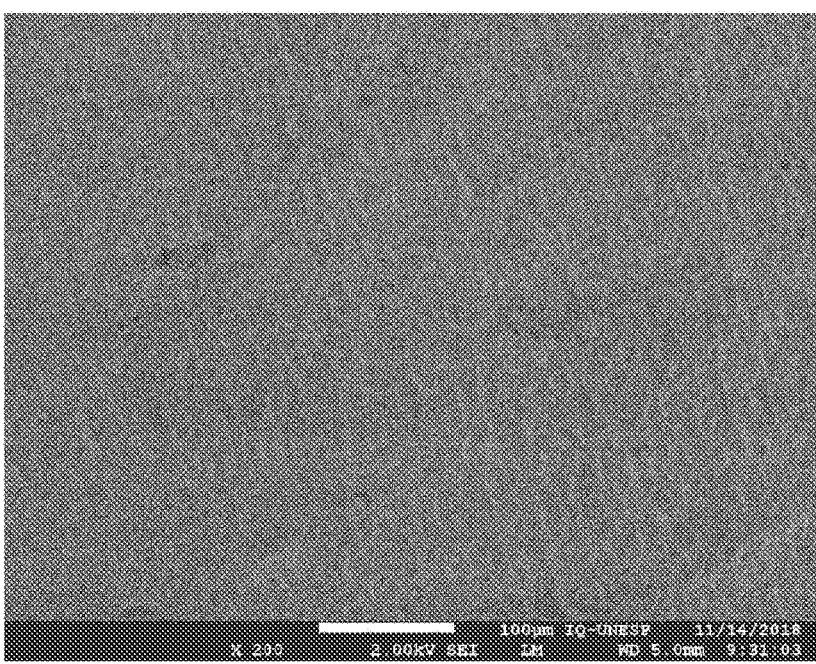
FIG. 10: A Scanning Electron Microscope image (200×) of a standard bovine pericardium sample.
Figure 11:
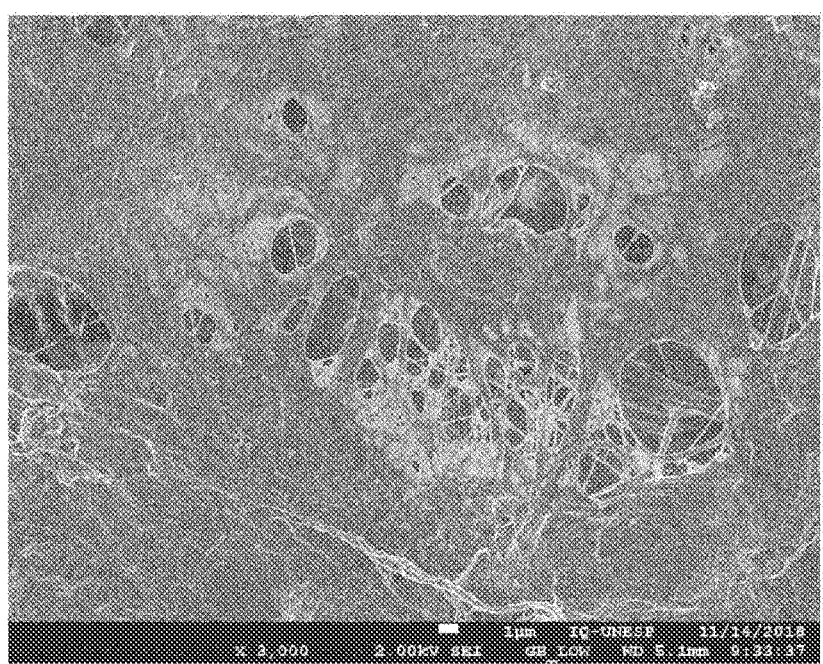
FIG. 11: A Scanning Electron Microscope image (3000×) of a standard bovine pericardium sample.
Figure 12:
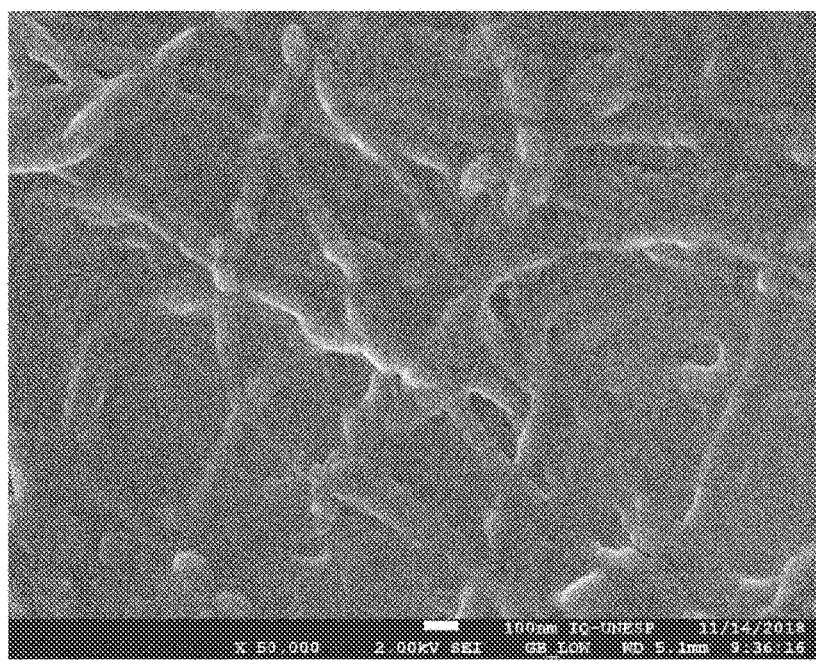
FIG. 12: A Scanning Electron Microscope image (50000×) of a standard bovine pericardium sample.
Figure 13:
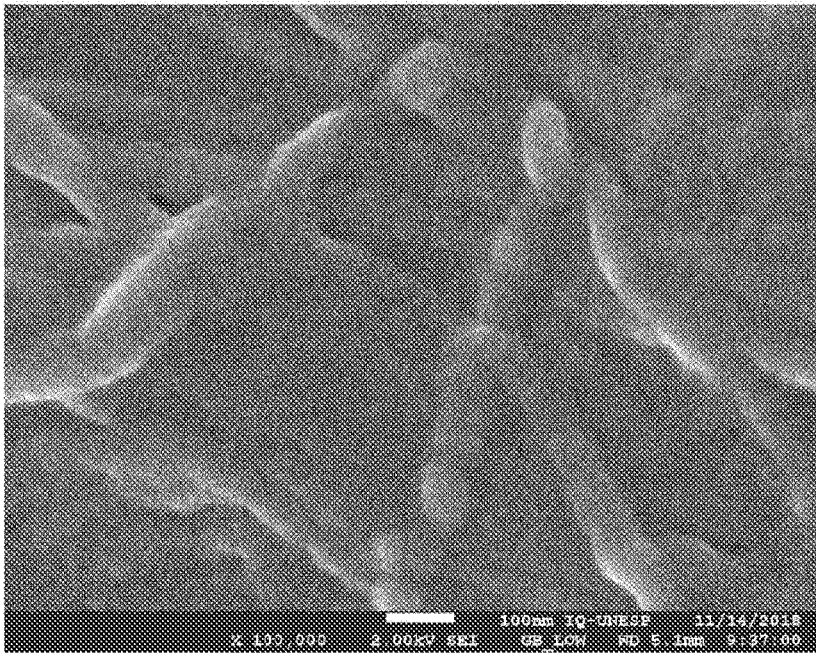
FIG. 13: A Scanning Electron Microscope image (100000×) of a standard bovine pericardium sample.

The collagen structure and the anticalcification effects of drying process of standard and dried (both) bovine pericardium have been evaluated by Scanning Electron Microscopy (SEM, FESEM, JEOL, model 7500F) using different resolutions:

(a) dried bovine pericardium: FIG. 6: 200× magnification; FIG. 7: 3000× magnification; FIG. 8: 50000× magnification; FIG. 9: 100000× magnification;

(b) standard bovine pericardium: FIG. 10: 200× magnification; FIG. 11: 3000× magnification; FIG. 12: 50000× magnification; FIG. 13: 100000× magnification.

The invention claimed is:

1. A method of treating biological tissue comprising the steps of:

(1) soaking the biological tissue treated with a crosslinking agent with a saline solution;

(2) subsequent to step (1), contacting the biological tissue with an aqueous solution comprising Hydrogen Peroxide;

(3) subsequent to step (2), contacting the biological tissue with an aqueous solution comprising PBS and EDTA;

(4) subsequent to step (3), contacting the biological tissue with a solution comprising glycerol, ethanol and EDTA; and (5) subsequent to step (4), contacting the biological tissue with a glycerol solution.

2. The method of claim 1, wherein the method further comprises the steps:

(3a) subsequent to step (3) and prior to step (4), contacting the biological tissue with ethanol with a concentration of at least 70% by volume; and (5a) subsequent to step (5), contacting the biological tissue with ethanol with a concentration of at least 70% by volume.

3. The method of claim 1, wherein the crosslinking agent is glutaraldehyde.

4. The method according to claim 1, wherein the biological tissue is one of bovine pericardium, porcine pericardium, and a heart valve.

5. The method according to claim 1, wherein the saline solution is an aqueous solution comprising 0.9% of sodium chloride.

6. The method according to claim 1, wherein a volume ratio of glycerol:ethanol in step (4) is from 1:5 to 5:1.

7. The method according to claim 1, wherein the EDTA in steps (3) and (4) has a concentration of 0.01% to 10.0% by weight.

8. The method according to claim 1, wherein the method further comprises the steps of:

(6) subsequent to step (5), drying the biological tissue;

(7) subsequent to step (6), placing the biological tissue in a package;

(8) subsequent to step (7), sealing the package; and (9) subsequent to step (8), sterilizing the package.

9. The method according to claim 8, wherein the sterilizing of the package comprising the biological tissue is carried out by exposing the package to ethylene oxide gas.

10. The method according to claim 8, wherein the steps (1) to (5) are carried out at a temperature of 10° C. to 25° C. and wherein the steps (6) and (7) are carried out at a temperature of 10° C. to 25° C.

11. The method according to claim 1, wherein the steps (1) to (5) are carried out at a temperature of 10° C. to 25° C.

12. The method according to claim 1, wherein the steps (4) and (5) are carried out while stirring for at least a total of 60 minutes during the performance of steps (4) and (5).

13. The method according to claim 1, wherein the hydrogen peroxide in step (2) has a concentration of 0.05% to 5.0% by volume.

* * * * *